(12) United States Patent
Shirley et al.

(10) Patent No.: US 7,067,485 B2
(45) Date of Patent: *Jun. 27, 2006

(54) IGF-I COMPOSITION AND ITS USE

(75) Inventors: Bret A. Shirley, Concord, CA (US);
Maninder S. Hora, Danville, CA (US)

(73) Assignee: Chiron Corporation, Emeryville, CA (US)

( * ) Notice: Subject to any disclaimer, the term of this patent is extended or adjusted under 35 U.S.C. 154(b) by 77 days.

This patent is subject to a terminal disclaimer.

(21) Appl. No.: 09/187,661

(22) Filed: Nov. 6, 1998

(65) Prior Publication Data

US 2003/0109427 A1 Jun. 12, 2003

Related U.S. Application Data

(60) Provisional application No. 60/096,081, filed on Aug. 11, 1998, provisional application No. 60/064,891, filed on Nov. 7, 1997.

(51) Int. Cl.
*A61K 38/00* (2006.01)
*A61K 38/30* (2006.01)
*C07K 14/00* (2006.01)

(52) U.S. Cl. ............ 514/12; 514/634; 530/399; 530/300; 530/303; 530/324

(58) Field of Classification Search ............ 514/2, 514/3, 4, 12, 634; 530/350, 300, 324, 303, 530/399
See application file for complete search history.

(56) References Cited

U.S. PATENT DOCUMENTS 5,324,639 A    6/1994  Brierley et al.
5,410,026 A *  4/1995  Chang et al. ............ 530/408

FOREIGN PATENT DOCUMENTS

EP    0 297 860 A1    1/1989
EP    0 440 989 A1    8/1991
WO    WO 96/40776     12/1996

OTHER PUBLICATIONS

Johnson et al., A Month Long Effect from a Single Injection of Microencapsulated Human Growth Hormone. Nature Medicine, vol. 2, No. 7, Jul. 1996.*
Johnson, et al., "A Month-Long Effect from a Single Injection of Microencapsulated Human Growth Hormone", *Nature Medicine*, vol. 2, No. 7, Jul. 1996.

* cited by examiner

*Primary Examiner*—Jon Weber
*Assistant Examiner*—Chih-Min Kam
(74) *Attorney, Agent, or Firm*—Roberta L. Robins; Alisa A. Harbin; Young J. Suh

(57) ABSTRACT

A highly concentrated, low salt-containing, biologically active syrup form of IGF-I or variant thereof and methods for its preparation are provided. This novel syrup form of IGF-I has an IGF-I concentration of at least about 250 mg/ml, a density of about 1.0 g/ml to about 1.2 g/ml, and a viscosity of about 13,000 centipoise (cps) to about 19,000 cps, as measured at ambient temperature (23° C.). The IGF-I syrup is prepared by precipitating or partitioning IGF-I from solution, preferably by adjusting the solution pH or by use of a solubility enhancer to concentrate IGF-I in solution followed by removal of the solubility enhancer. The precipitated syrup is useful as a means of storing IGF-I in a stable form and as a means of preparing compositions comprising biologically active IGF-I. Pharmaceutical compositions and kits comprising this concentrated IGF-I syrup are provided. The precipitated IGF-I syrup, IGF-I reconstituted from the IGF-I syrup, pharmaceutical compositions, and kits are useful in IGF-I therapy directed to IGF-I-responsive conditions.

32 Claims, 2 Drawing Sheets

IGF-I COMPOSITION AND ITS USE

CROSS-REFERENCE TO RELATED APPLICATIONS

This application claims benefit of U.S. Provisional Application No. 60/064,891, filed Nov. 7, 1997, and claims benefit of U.S. Provisional Application No. 60/096,081, filed Aug. 11, 1998.

FIELD OF THE INVENTION

The present invention relates to a novel composition of IGF-I and variants thereof.

BACKGROUND OF THE INVENTION

Insulin-like growth factor I (IGF-I) is a 70-amino-acid polypeptide hormone having insulin-like and mitogenic growth biological activities (Rinderknecht (1978) *J. Biol. Chem.* 253:2769; Rinderknecht (1978) *FEBS Lett.* 89:283). This hormone enhances growth and/or survival of cells in a variety of tissues including musculoskeletal systems, liver, kidney, intestines, nervous system tissues, heart, and lung. Administration of IGF-I has been indicated for the treatment of a variety of conditions in humans and animals.

Various formulations of IGF-I have been made. See, for example, U.S. Pat. Nos. 5,126,324, 5,324,639, 5,324,660, 5,374,620, and 5,650,496; International Publication Nos. WO 94/15584 and WO 96/40776; copending application entitled "High and Low Load Formulation of IGF-I in Multivesicular Liposomes," U.S. patent application Ser. No. 08/925,531, filed Sep. 8, 1997; copending application entitled "Injectable Formulation Containing Succinate," U.S. patent application Ser. No. 60/080,008, filed Apr. 3, 1998; and copending application filed concurrently herewith entitled "Method for Producing Sustained-Release Formulations," U.S. patent application Ser. No. 09/188,051.

Inclusion bodies containing IGF-I have been formed when IGF-I is expressed as a heterologous protein. See, for example, European Patent Nos. EP 123,228, EP 128,733, EP 135,094, EP 230,869, and EP 288,451. When incorporated into such inclusion bodies, IGF-I is in a generally misfolded and biologically inactive form, and must be reduced, refolded, and resolubilized into an active, solubilized form. See, for example, U.S. Pat. Nos. 5,288,931, 5,410,026, 5,663,304, and 5,756,672; and International Publication No. WO 91/02807.

Other methods of making highly concentrated forms of proteins involve use of protein solubilizers and precipitating agents such as salts, and/or various manipulations of solution conditions such as pH, temperature, ionic strength, and other techniques known in the art. These methods often lead to protein preparations that are undesirable because they are biologically inactive, are relatively dilute, and/or contain pharmaceutically undesirable salts or other agents.

SUMMARY OF THE INVENTION

A highly concentrated, low salt-containing, biologically active form of IGF-I or variant thereof and methods for its preparation are provided. This novel form of IGF-I, which is obtained according to the methods of the invention, has the consistency of a viscous "syrup". This syrup has an IGF-I concentration of at least about 250 mg/ml, a density of about 1.0 g/ml to about 1.2 g/ml, and a viscosity of about 13,000 centipoise (cps) to about 19,000 cps, as measured at ambient temperature (23° C.). When reconstituted from the syrup form, IGF-I is biologically active without the need for refolding. The IGF-I syrup is prepared by precipitating IGF-I from solution, by, for example, appropriately adjusting the solution pH or by removal of a solubility enhancer.

The highly concentrated IGF-I syrup is useful as a means of storing IGF-I in a stable form and as a means for preparing compositions comprising biologically active IGF-I. Thus, the IGF-I syrup, or IGF-I reconstituted from this syrup, may be incorporated into other substances to form such compositions, as, for example, pharmaceutical preparations such as sustained-release formulations and delivery devices. Pharmaceutical compositions comprising this concentrated IGF-I syrup are provided. Kits comprising IGF-I in this highly concentrated syrup form and a separate pharmaceutically acceptable biological buffer are also provided. The IGF-I syrup, IGF-I reconstituted from the syrup, pharmaceutical compositions, and kits are useful in IGF-I therapy directed to IGF-I-responsive conditions.

DETAILED DESCRIPTION OF THE INVENTION

Figure 1:
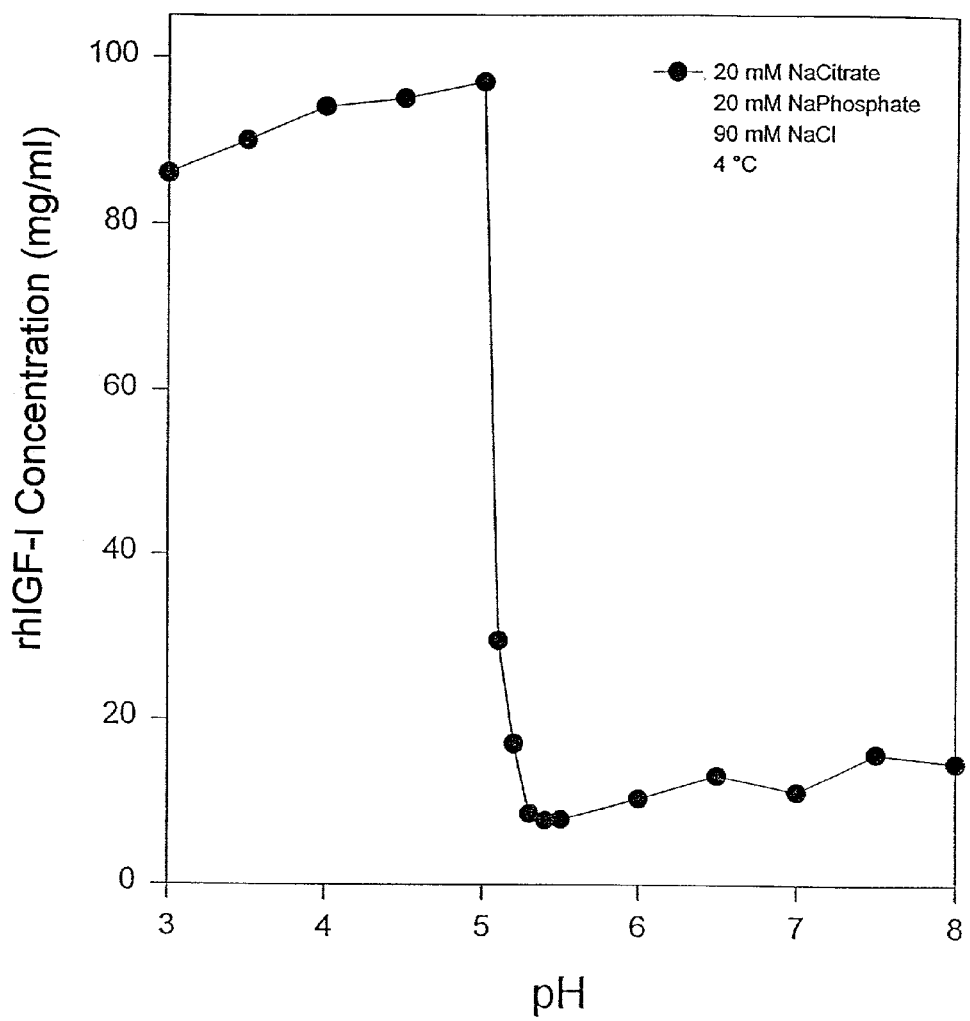
FIG. 1 shows rhIGF-I solubility as a function of pH.

The present invention is directed to a novel form of IGF-I or variant thereof and methods for its preparation. This highly concentrated, low salt-containing, biologically active form of IGF-I or variant thereof has the consistency of a viscous "syrup", hereinafter referred to as a syrup. Methods for preparing this novel form of IGF-I or a variant thereof are disclosed. The IGF-I syrup is prepared by precipitating IGF-I from solution, preferably by appropriately adjusting the solution pH or by addition of an appropriate solubilizing agent to concentrate IGF-I in solution followed by removal of the solubilizing agent. The resulting syrup form of IGF-I or variant thereof provides a means for packaging greater amounts of IGF-I within a given volume. The ramifications of these are the basis for the compositions and other methods disclosed in the present invention that are useful for IGF-I therapy directed to IGF-I-responsive conditions.

The term "IGF-I" as used herein refers to insulin-like growth factor I (IGF-I), a single chain peptide having 70 amino acids and a molecular weight of about 7,600 daltons. IGF-I stimulates mitosis and growth processes associated with cell development.

Although the following description of the IGF-I syrup form, methods for its preparation, and uses thereof refers to IGF-I, compositions and methods of the present invention encompass both IGF-I and IGF-I variants as defined below.

By "highly concentrated" is intended an IGF-I concentration of at least about 250 mg/ml, for example, at least about 300 mg/ml, or at least about 350 mg/ml, or at least about 425 mg/ml, or about 450 mg/ml to 500 mg/ml, as measured at ambient temperature (23° C.). At these concentrations and temperature, this syrup has a density of about 1.0 g/ml to about 1.2 g/ml, more preferably about 1.1 g/ml, and a viscosity of about 13,000 cps to about 19,000 cps, preferably about 14,000 cps to about 18,000 cps, more preferably about 15,000 cps to about 17,000 cps, still more preferably about 15,500 cps to about 16,500 cps, even more preferably about 16,000 cps. This is a substantially lower viscosity than the viscosity of IGF-I formed in inclusion bodies. In one embodiment, the syrup has an IGF-I concentration of about 350 mg/ml, a density of about 1.07 g/ml, and a viscosity of about 15,700 cps, as measured at ambient temperature. By "low salt-containing" is intended an amount of salt that is insufficient to cause precipitation of the protein. "Biologically active" is intended to mean that the IGF-I or variant, when reconstituted from its syrup form into a solution form, is biologically active without the need for refolding.

This highly concentrated IGF-I syrup is obtained by precipitating IGF-I or variant thereof in accordance with the methods of the present invention. This syrup form of IGF-I is flowable and clear to opalescent in appearance, features that distinguish it from salt-precipitated forms of IGF-I, such as IGF-I prepared by precipitation or "salting out" using, for example, ammonium sulfate. As a result of the high solubility of ammonium sulfate (3.9 M in water at 0° C.), high ionic strength solutions favoring IGF-I precipitation can readily be achieved. See, for example, Voet and Voet (1995) *Biochemistry* (John Wiley and Sons, New York), pp. 79–81. This method results in precipitation of a salt-protein complex that is white in appearance, has the consistency of a thick paste, and has a substantially higher viscosity than the IGF-I syrup of the present invention. Such a precipitated salt-protein complex is not amenable to quick and easy recovery of low salt-containing IGF-I. To retrieve low salt-containing IGF-I, the precipitate would have to be resolubilized (and thereby made less concentrated), followed by removal of salt from the protein solution.

Preparation of the highly concentrated IGF-I syrup of the present invention is preferably carried out in accordance with the methods of the present invention. These methods involve manipulation of solution pH or addition of a solubilizing agent to enhance solubility of IGF-I followed by removal of the solubilizing agent to create the IGF-I syrup. Both of these methods allow for precipitation of IGF-I into a highly concentrated, low salt-containing syrup that can readily be reconstituted to recover a solution of biologically active protein.

The first of these methods is based upon observations of the unusual solubility properties of IGF-I. IGF-I is very soluble below pH 5.0, where concentrations of 50–200 mg/ml can be obtained. However, a sharp decrease in solubility is observed between pH 5.0 and pH 5.5. Above pH 5.5, the solubility of IGF-I is less than 10 mg/ml (see FIG. 1).

This method of preparing the highly concentrated IGF-I syrup comprises reducing the solubility of IGF-I such that IGF-I precipitates from a buffer solution containing IGF-I. Precipitation is achieved by adjusting the pH of the IGF-I-containing buffer solution to a pH above about pH 5.0 as disclosed below.

Accordingly, IGF-I is prepared within a suitable buffer solution whose critical characteristic is an initial pH that favors solubility of IGF-I. The buffer solution may be any buffer that provides the desired initial pH. A number of suitable buffers are available in the art, including, but not limited to, succinate buffer, phosphate buffer, citrate buffer, acetic acid buffer, an acetic acid salt buffer such as sodium acetate or potassium acetate, and the like. In one embodiment of the invention, the buffer is acetic acid. Any buffer can be used as long as the initial pH promotes IGF-I solubility.

The buffer solution containing IGF-I will have an initial pH of less than about pH 5.0, preferably about pH 2.0 to about pH 5.0, more preferably about pH 3.0 to about pH 4.5, even more preferably about pH 3.5 to about pH 4.0. The initial concentration of IGF-I in this low-pH buffer solution will determine the amount of the highly concentrated IGF-I syrup obtained following upward adjustment of pH. Thus, a higher initial concentration of IGF-I will yield a greater amount of precipitated IGF-I syrup. Because solubility of IGF-I decreases sharply at solution pH greater than about pH 5.0, an initial solution pH in the range less than about 5.0 is preferable to maximize the initial concentration of IGF-I in the buffer solution and therefore maximize yield of precipitated syrup. Regardless of the initial concentration of IGF-I, the concentration of the precipitated IGF-I syrup is at least about 250 mg/ml as noted above.

In order to obtain this highly concentrated IGF-I syrup, the initial pH of the buffer solution containing IGF-I is adjusted upward to a final pH greater than about pH 5.0, preferably to a pH of greater than about pH 5.0 to about pH 9.0, more preferably to a pH of greater than about pH 5.0 to about pH 8.0, still more preferably to a pH of about pH 5.5 to about pH 7.0, even more preferably to a pH of about pH 5.5 to about pH 6.5, and most preferably to a pH of about pH 5.5 to about pH 6.0. As pH is increased, IGF-I above the solubility limit at the higher pH conditions precipitates, forming a viscous syrup. pH of the buffer solution may be adjusted by standard titrating procedures well known in the art, such as with addition of sodium hydroxide. Alternatively, solution pH may be adjusted by dialyzing the initial buffer solution containing IGF-I against any suitable buffer solution having the desired final pH above pH 5.0 as disclosed above. Such buffers include, for example, inorganic (e.g., phosphate) and organic (e.g., acetate) buffers. In one embodiment of the invention, the IGF-I buffer solution having an initial pH less than or equal to pH 5.0 is dialyzed against a sodium citrate buffer at pH 6.0.

For example, when a solution containing 100 mg/ml IGF-I at an initial pH 4.0 is adjusted to a final pH of 6.0, only 8.0 mg/ml IGF-I remains in solution while the remaining 92 mg/ml precipitates, forming a highly concentrated IGF-I syrup. The IGF-I syrup can be separated from the buffered solution by decanting or suctioning off the solution. This syrup has a concentration of IGF-I of at least about 250 mg/ml, as disclosed above.

This highly concentrated IGF-I syrup represents a precipitated form of IGF-I. For some proteins, precipitation results from a denaturation and/or aggregation reaction that is irreversible, leading to protein inactivation. In the case of the precipitated IGF-I of the present invention, the precipitation reaction is reversible. Thus, the IGF-I syrup can be reconstituted, and the recovered soluble IGF-I retains full biological activity when compared to the biological activity of IGF-I that has not undergone precipitation by the method of the present invention. Layering a buffer solution over known aliquots of syrup allows for the IGF-I to reconstitute. Any suitable buffer solution may be used for reconstitution, as long as the buffering capacity maintains solution pH in a range that allows for IGF-I solubility. As IGF-I solubility is a function of pH, greater amounts of soluble IGF-I can be recovered from the concentrated IGF-I syrup using a given volume of buffer solution when solution pH is below about pH 5.0 than can be recovered when solution pH is above about pH 5.0.

The highly concentrated IGF-I syrup of the present invention can also be prepared using an appropriate solubilizing agent or so-called solubility enhancer. For purposes of the present invention, "solubility enhancer" refers to a compound that includes a guanidinium group and that is capable of enhancing the solubility of IGF-I or a variant of IGF-I. Examples of such solubilizing agents include the amino acid arginine, as well as amino acid analogues of arginine that retain the ability to enhance solubility of IGF-I at pH 5.5 or greater. Such analogues include, without limitation, dipeptides and tripeptides that contain arginine. Other suitable solubilizing agents include, without limitation, guanidine-containing compounds such as guanidine carbaniedine, guanidine acetate, guanidine amine, guanidine carbonate, guanidine 1-cyano, guanidine 1,3-diphenyl, guanidine 1,3-di(2-toyl), guanidine hydrochloride, guanidine nitrate, 1-nitroguanidine, guanidine picrate, guanidine thiocyanate, guanidine tetraphenyl, guanidine 1,1,3-triphenyl, guanidine 1,2,3-triphenyl, guanidine 1-ureido, agmatine, 4-guanidinobenzoic acid, guanidoacetic acid, guanidinosuccinic acid, guanethidine, 4'acetamidophenyl 4-guanidinobenzoate, 2-iminobiotin, N-(2-guanidinoethyl)-5-isoquinolinesulfonamide, guaninobutyric acid, guanidinopropionic acid, and the like, commercially available from, e.g., Sigma Chemical Company, St. Louis, Mo. Of these compounds, arginine, guanidine hydrochloride, agmatine, 4-guanidinobenzoic acid, guanidoacetic acid, and guanidinosuccinic acid, are preferred.

By "enhancing the solubility" of IGF-I is intended increasing the amount of IGF-I that can be dissolved in solution at pH 5.5 or greater, pH 6.0 or greater, pH 7.0 or greater, pH 8.0 or greater, or pH 9.0 or greater in the presence of a guanidinium-containing compound compared to the amount of IGF-I that can be dissolved at pH 5.5 or greater, pH 6.0 or greater, pH 7.0 or greater, pH 8.0 or greater, or pH 9.0 or greater in a solution with the same components but lacking the guanidinium-containing compound. The ability of a guanidinium-containing compound to enhance the solubility of IGF-I can be determined using methods well known in the art. In general, the concentration of the solubilizing agent added to solution will be from about 10 mM to about 1 M, preferably about 15 mM to about 500 mM, and more preferably, for example, in the case of the compound arginine, in a concentration range of about 20 mM to about 200 mM, as disclosed in the copending application filed concurrently herewith entitled "*Compositions Providing for Increased IGF-I Solubility,*" U.S. patent application Ser. No. 09/188,051.

In this manner, addition of a solubility enhancer to solution allows for the preparation of a high concentration IGF-I solution. The solubility enhancer is then removed from this IGF-I solution by dialysis or diafiltration. Removal of the solubility enhancer results in precipitation of IGF-I in the highly concentrated syrup form. The soluble portion of IGF-I can then be decanted off and the IGF-I syrup recovered. Again, when reconstituted in solution, the IGF-I is biologically active without the need for refolding.

The IGF-I to be prepared in a highly concentrated form according to the methods of the present invention can be from any animal species including, but not limited to, avian, canine, bovine, porcine, equine, and human. Preferably the IGF-I is from a mammalian species when the concentrated form is to be used in treatment of a mammalian IGF-I-responsive disorder, and more preferably is from a mammal of the same species as the mammal undergoing treatment for such a disorder. It is recognized that the IGF-I can be made by recombinant methods using the corresponding coding sequence for IGF-I from the animal species of interest. Such recombinant methods are discussed in more detail below.

Biologically active variants of IGF-I are also encompassed by the method of the present invention. Such variants should retain IGF-I activities, particularly the ability to bind to IGF-I receptor sites. IGF-I activity may be measured using standard IGF-I bioassays. Representative assays include known radioreceptor assays using placental membranes (see, e.g., U.S. Pat. No. 5,324,639; Hall et al. (1974) *J. Clin. Endocrinol. and Metab.* 39:973–976; and Marshall et al. (1974) *J. Clin. Endocrinol. and Metab.* 39:283–292), a bioassay that measures the ability of the molecule to enhance incorporation of tritiated thymidine, in a dose-dependent manner, into the DNA of BALB/c 3T3 fibroblasts (see, e.g., Tamura et al. (1989) *J. Biol. Chem.* 262:5616–5621), and the like; herein incorporated by reference. Preferably, the variant has at least the same activity as the native molecule.

Suitable biologically active variants can be IGF-I fragments, analogues, and derivatives. By "IGF-I fragment" is intended a protein consisting of only a part of the intact IGF-I sequence and structure, and can be a C-terminal deletion or N-terminal deletion of IGF-I. By "analogues" is intended analogues of either IGF-I or an IGF-I fragment that comprise a native IGF-I sequence and structure having one or more amino acid substitutions, insertions, or deletions. Peptides having one or more peptoids (peptide mimics) are also encompassed by the term analogue (see International Publication No. WO 91/04282). By "derivatives" is intended any suitable modification of IGF-I, IGF-I fragments, or their respective analogues, such as glycosylation, phosphorylation, or other addition of foreign moieties, so long as the IGF-I activity is retained. Methods for making IGF-I fragments, analogues, and derivatives are available in the art. See generally U.S. Pat. Nos. 4,738,921, 5,158,875, and 5,077,276; International Publication Nos. WO 85/00831, WO 92/04363, WO 87/01038, and WO 89/05822; and European Patent Nos. EP 135094, EP 123228, and EP 128733; herein incorporated by reference.

IGF-I variants will generally have at least 70%, preferably at least 80%, more preferably about 90% to 95% or more, and most preferably about 98% or more amino acid sequence identity to the amino acid sequence of the reference IGF-I molecule. A variant may differ by as few as 10, as few as 5, as few as 4, 3, 2, or even 1 amino acid residue. By "sequence identity" is intended the same amino acid residues are found within the IGF-I variant and the reference IGF-I molecule when a specified, contiguous segment of the amino acid sequence of the variant is aligned and compared to the amino acid sequence of the reference molecule. Methods for determining identity between sequences are well known in the art. See, for example, the ALIGN program (Dayhoff (1978) in *Atlas of Protein Sequence and Structure* 5:Suppl. 3 (National Biomedical Research Foundation, Washington, D.C.) and programs in the Wisconsin Sequence Analysis Package, Version 8 (available from Genetics Computer Group, Madison, Wis.), for example, the GAP program. For purposes of optimal alignment of the two sequences, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least twenty (20) contiguous nucleotides, and may be 30, 40, 50, 100, or more nucleotides. Corrections for increased sequence identity associated with inclusion of gaps in the variant's amino acid sequence can be made by assigning gap penalties. Methods of sequence alignment are well known in the art.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Meyers and Miller (1988) *Computer Applic. Biol. Sci.* 4:11–17.

The art provides substantial guidance regarding the preparation and use of such IGF-I variants, as discussed further below. A fragment of IGF-I will generally include at least about 10 contiguous amino acid residues of the full-length molecule, preferably about 15–25 contiguous amino acid residues of the full-length molecule, and most preferably about 20–50 or more contiguous amino acid residues of full-length IGF-I. In preparing the IGF-I variants, one of skill in the art can readily determine which modifications to the native protein nucleotide or amino acid sequence will result in a variant that enables preparation of the highly concentrated form of the IGF-I variant in accordance with the methods disclosed in the present invention. These will generally be conservative amino acid substitutions that preserve the charge of the substituted residue (e.g., aspartic acid for glutamic acid).

Several IGF-I variants are known in the art and include those described in, for example, *Proc. Natl. Acad. Sci. USA* 83 (1986):4904–4907; *Biochem. Biophys. Res. Commun.* 149 (1987):398–404; *J. Biol. Chem.* 263 (1988):6233–6239; *Biochem. Biophys. Res. Commun.* 165 (1989):766–771; Forsbert et al. (1990) *Biochem. J.* 271:357–363; U.S. Pat. Nos. 4,876,242 and 5,077,276; and International Publication Nos. WO 87/01038 and WO 89/05822. Representative variants include one with a deletion of Glu-3 of the mature molecule, a variant with up to 5 amino acids truncated from the N-terminus, a variant with a truncation of the first 3 N-terminal amino acids (referred to as des(1–3)-IGF-I, des-IGF-I, tIGF-I, or brain IGF), and a variant including the first 17 amino acids of the B chain of human insulin in place of the first 16 amino acids of human IGF-I.

The IGF-I used in making the highly concentrated syrup form of IGF-I according to the present invention can be in its substantially purified, native, recombinantly produced, or chemically synthesized forms. For example, the IGF-I can be isolated directly from blood, such as from serum or plasma, by known methods. See, for example, Phillips (1980) *New Eng. J Med.* 302:371–380; Svoboda et al. (1980) *Biochemistry* 19:790–797; Cornell and Boughdady (1982) *Prep. Biochem.* 12:57; Cornell and Boughdady (1984) *Prep. Biochem.* 14:123; European Patent No. EP 123,228; and U.S. Pat. No. 4,769,361. Alternatively, IGF-I can be synthesized chemically, by any of several techniques that are known to those skilled in the peptide art. See, for example, Li et al. (1983) *Proc. Natl. Acad. Sci. USA* 80:2216–2220, Stewart and Young (1984) *Solid Phase Peptide Synthesis* (Pierce Chemical Company, Rockford, Ill.), and Barany and Merrifield (1980) *The Peptides: Analysis, Synthesis, Biology,* ed. Gross and Meienhofer, Vol. 2 (Academic Press, New York, 1980), pp. 3–254, for solid phase peptide synthesis techniques; and Bodansky (1984) *Principles of Peptide Synthesis* (Springer-Verlag, Berlin); and Gross and Meienhofer, eds. (1980) *The Peptides: Analysis, Synthesis, Biology,* Vol. 1 (Academic Press, New York), for classical solution synthesis. IGF-I can also be chemically prepared by the method of simultaneous multiple peptide synthesis. See, for example, Houghten (1985) *Proc. Natl. Acad. Sci. USA* 82:5131–5135; and U.S. Pat. No. 4,631,211. These references are herein incorporated by reference.

Genetic engineering by recombinant DNA techniques can be the most efficient way of producing IGF-I. The human DNA sequence encoding IGF-I is known and can be introduced into host cells for expression. IGF-I can be produced by recombinant DNA techniques in *E. coli*, yeast, insect, and mammalian cells. Secreted IGF-I can be made by adding a signal sequence to the DNA sequence encoding IGF-I. In addition, the DNA sequence encoding IGF-I can be manipulated to make IGF-I fragments, analogues, or derivatives. Such recombinant DNA techniques are generally available in the art. See, for example, International Publication No. WO 96/07424, where recombinant human IGF-I protein is produced in yeast.

Having provided methods for preparing this highly concentrated IGF-I syrup, the syrup itself has several uses as disclosed in the present invention. First, the syrup provides a means for packaging high concentrations of IGF-I within small volume spaces. Hence, the syrup provides an easier means of storage of IGF-I. When stored in an appropriate container, aliquots of the syrup can be reconstituted using a suitable buffer solution to recover soluble IGF-I that retains its biological activity. Storage of the IGF-I syrup is preferably at a temperature of about 2° C. to about 10° C., more preferably about 2° C. to about 8° C., most preferably at about 4° C. Storage in this manner provides a shelf life of 18 to 24 months or more. Additionally, the IGF-I syrup can be formulated with protein stabilizers in order to preserve the activity thereof. Such stabilizers are known in the art and include, e.g., simple salts, buffer salts, polyhydroxylated compounds such as glycerol, mannitol, sucrose and polyethylene glycols, and surfactants. See, e.g., International Publication No. WO 92/11844.

Containers comprising the highly concentrated IGF-I syrup can be packaged in kit form for subsequent preparation of pharmaceutical compositions useful in IGF-I therapy. Such a kit additionally comprises a suitable buffer for reconstituting the highly concentrated syrup form of IGF-I. The resulting reconstituted IGF-I can be used in formulating a pharmaceutical composition as outlined below. The pharmaceutical composition is formulated with a known concentration of IGF-I such that administration of a therapeutically effective dose promotes a desired therapeutic response with respect to a particular IGF-I responsive condition undergoing therapy. By "desired therapeutic response" is intended an improvement in the condition or in the symptoms associated with the condition.

The syrup form of IGF-I is useful as a means of preparing compositions that comprise IGF-I. In this manner, the IGF-I syrup may be directly incorporated into one or more substances to form a composition that comprises biologically active IGF-I in a highly concentrated form. Alternatively, aliquots of the IGF-I syrup may serve as a source for reconstituted IGF-I, which may then be incorporated into one or more substances to form a composition comprising biologically active IGF-I in its reconstituted state. Of particular interest are pharmaceutical compositions and compositions comprising IGF-I in an encapsulated state that is useful, for example, in formulating sustained-release pharmaceutical compositions.

The highly concentrated IGF-I syrup of the present invention is useful in IGF-I therapy directed to any IGF-I-responsive condition when administered to a therapeutic site undergoing therapy for such a condition. Thus, IGF-I in its syrup form, or IGF-I reconstituted from the IGF-I syrup, may be incorporated into one or more substances to form a pharmaceutical composition that is then placed in contact with the therapeutic site. Administering a therapeutically effective amount of such a composition promotes a desired therapeutic response with respect to an IGF-I-responsive condition undergoing IGF-I therapy. The preferred form of IGF-I, i.e., syrup or reconstituted, depends upon the preferred method of delivery of the pharmaceutical composition, as outlined below.

Suitable methods of delivery of the pharmaceutical composition comprising the concentrated IGF-I syrup include, but are not limited to, gel formulations, viscous solutions, sustained-release formulations, implant delivery systems, such as pumps, and the like. Such delivery systems allow for the controlled and concentrated delivery of IGF-I to a therapeutic site. The exact formulation employed will depend on the type of application that is desired. For example, gel formulations may be utilized for topical or incisional wound healing, whereas low viscosity, aqueous formulations may be used for those applications requiring a more fluid formulation having a higher water content.

The highly concentrated IGF-I syrup of the invention can be used in gel formulations to provide a controlled-delivery system. By "controlled delivery" is intended drug release sufficient to maintain a therapeutic level over an extended period of time up to several months. The concentrated IGF-I syrup of the present invention can be utilized in formulations to increase the residence time of the growth factor and provide a sustained-release dosage form. This is an important advantage as it permits less frequent application of the formulation to the therapeutic site and thereby permits less disturbance of the wound or site and its cellular components. See, for example, U.S. Pat. Nos. 5,705,485, 5,457,093, 3,934,013, and 5,071,644.

The gel formulations of the invention include those containing a water soluble, pharmaceutically acceptable polymeric material. See, for example, U.S. Pat. No. 5,705,485.

The concentrated IGF-I of the invention can also be used in sustained-release pharmaceutical compositions, which prolong the presence of IGF-I in the treated mammal, generally for longer than one day. A sustained-release pharmaceutical composition generally provides the pharmaceutical composition within a polymer, preferably a hydrophilic polymer for sustained-release of the drug. Many methods of preparation of a sustained-release formulation are known in the art and are disclosed in Remington's Pharmaceutical Sciences (18$^{th}$ ed.; Mack Pub. Co.: Eaton, Pa., 1990), herein incorporated by reference. Generally, the IGF-I can be entrapped in semipermeable matrices of solid hydrophobic polymers. The matrices can be shaped into films or microcapsules. Examples of such matrices include, but are not limited to, polyesters, copolymers of L-glutamic acid and gamma ethyl-L-glutamate (Sidman et al. (1983) Biopolymers 22:547–556), poly-actides (U.S. Pat. No. 3,773,919 and EP 58,481), polylactate polyglycolate (PLGA) hydrogels (see, for example, Langer et al. (1981) J. Biomed. Mater. Res. 15:167–277; Langer (1982) Chem. Tech. 12:98–105), non-degradable ethylene-vinyl acetate, degradable lactic acid-glycolic acid copolymers such as the Lupron Depot™, and poly-D-(–)-3-hydroxybutyric acid (EP 133, 988). Suitable microcapsules can also include hydroxymethylcellulose or gelatin-microcapsules and poly-methylmethacylate microcapsules prepared by coacervation techniques or by interfacial polymerization. In addition, microemulsions or colloidal drug delivery systems such as liposomes and albumin microspheres may also be used. See Remington's Pharmaceutical Sciences (18$^{th}$ ed.; Mack Pub. Co.: Eaton, Pa., 1990).

Such sustained-release pharmaceutical compositions are described, for example, in U.S. Pat. Nos. 4,178,361; 4,404, 183; 4,343,789; 5,614,487; 5,422,116; 4,309,405; 4,248, 858; 4,524,060; 4,973,470; 4,539,199; 4,309,406; 4,309, 404; 4,248,857; and 4,248,856; all of which are herein incorporated by reference. One such sustained-release composition where a polypeptide such as IGF-I is entrapped in biodegradable microparticles is described in the application filed concurrently herewith entitled "Method for Producing Sustained-Release Formulations," U.S. patent application Ser. No. 09/188,051, the entirety of which is herein incorporated by reference.

In one embodiment of the invention, the pharmaceutical composition comprising the highly concentrated IGF-I syrup is administered via local drug delivery. Local application of the drug affords concentrated delivery of the drug, achieving tissue levels not otherwise obtainable through other administration routes. As drug release occurs via diffusion, a time-dependent process, delivery to the target cite will be sustained for days to weeks or beyond, depending upon the delivery system utilized. Further, local delivery reduces systemic drug exposure, thereby limiting systemic side effects. It also allows for delivery of agents that might otherwise be difficult or impossible to deliver via oral or intravenous routes due to problems of solubility or formulation. Local administration also provides the possibility of utilizing agents that might not otherwise be administratable because of dosage range of toxicity limitations encountered with conventional routes of administration.

Means for local drug delivery include balloon catheter delivery systems, endovascular polymer-coated stents, facilitated diffusion, polymeric endoluminal paving, and controlled-release matrices. See, for example, Eccleston et al. (1995) Interventional Cardiology Monitor 1:33–40–41, and Slepian (1996) Intervente Cardiol. 1:103–116, herein incorporated by reference.

In a preferred embodiment, the highly concentrated IGF-I syrup is used in an implantable pump, such as the osmotically driven DUROS™ implantable pump from ALZA (Palo Alto, Calif.). Such pumps are surgical implants that provide for drug delivery over months (e.g., 6–12 months) in a continuous, steady-state fashion at a variety of doses. Because they are implanted, these pumps must be small to be practical. Reloading the pump most often requires additional surgery. The material loaded into them must therefore be highly concentrated to allow them to remain implanted for the maximum amount of time and to minimize the number of surgeries required to implant another device. The IGF-I syrup of the present invention provides a means of packaging high concentrations of IGF-I in the small volumes typical of such implant devices.

Alternatively, aliquots of the highly concentrated IGF-I syrup may be incorporated into liquid injectables for parenteral delivery. In this embodiment, an aliquot of the syrup is reconstituted as previously described using a pharmaceutically acceptable buffer having a buffering capacity that maintains solution pH in a range that allows for IGF-I solubility, preferably a pH below 5.0. The reconstituted IGF-I is then incorporated into a pharmaceutical composition comprising a pharmaceutically acceptable carrier as described below. Preferably the carrier is a carrier favorable for parenteral delivery, and preferably is isotonic with the blood of the recipient. Such carriers include, but are not limited to, water, saline, Ringer's solution, and dextrose solution. Other carriers are described below.

The pharmaceutical composition comprising reconstituted IGF-I should be formulated in a unit dosage and in an injectable or infusible form such as solution, suspension, or emulsion. It can also be in the form of lyophilized powder, which can be converted into solution, suspension, or emulsion before administration. The pharmaceutical composition comprising reconstituted IGF-I is preferably sterilized by membrane filtration and is stored in unit-dose or multi-dose containers such as sealed vials or ampules.

Any of the pharmaceutical compositions comprising the concentrated IGF-I syrup, or IGF-I reconstituted from the IGF-I syrup, as described above may contain other components that modulate the therapeutic treatment with IGF-I. Such components include any of the IGF-I binding proteins, IGF-I receptors, and the acid-labile subunit of the IGF-I binding complex. IGFBP-3 may enhance the stimulatory effect of IGF-I on proteoglycan synthesis (see Chevalier et al. (1996) *British J. Rheumat.* 35:515–522). In addition, an acid labile glycoprotein also has been shown to be associated with the protein complex formed by IGF-I and its binding proteins. Thus, the therapeutically effective pharmaceutical composition may contain such acid-labile glycoprotein and IGF-I binding proteins, when proven to facilitate the desired positive response on the IGF-I-responsive disorder undergoing treatment. The amount of IGFBPs to be administered with IGF-I can be determined according to the molar ratio between IGF-I and IGFBPs. This molar ratio can range from about 0.5:1 to about 3:1, preferably about 1:1 (see U.S. Pat. No. 5,187,151). Alternatively, the pharmaceutical composition may include agents that disrupt IGF-I binding to IGFBPs and which may be effective in increasing the amount of IGF-I present in the affected physiological site to a therapeutically effective level. In addition to these components, the pharmaceutical composition comprising IGF-I may include one or more protease inhibitors. An exemplary protease inhibitor is sodium pentosan polysulfate (PPS), a polysulfated polysaccharide. This protease inhibitor has efficacy in treating osteoarthritis in combination with low dosages of IGF-I (1 µg IGF-I intra-articularly 3 times per week) (Rogachefsky et al. (1993) *Osteoarthritis and Cartilage* 1:105–114). Such a protease inhibitor can be administered by other routes, such as intramuscularly, during administration of the effective dose of IGF-I.

The pharmaceutical composition in accordance with the present invention may further comprise one or more other therapeutic agents that are effective in treating other disorders in the individual, as long as the biochemical actions of the additional therapeutic agents do not interfere with the efficacy of intended action of the IGF-I treatment. Examples of such agents include, but are not limited to, antibiotics, anti-inflammatory agents, and the like.

A pharmaceutically acceptable carrier should be mixed with the IGF-I and other components used in preparing the pharmaceutical composition. By "pharmaceutically acceptable carrier" is intended a carrier that is conventionally used in the art to facilitate the storage, administration, and/or the healing effect of the therapeutic ingredients. A carrier may also reduce any undesirable side effects of the IGF-I. A suitable carrier should be stable, i.e., incapable of reacting with other ingredients in the formulation. It should not produce significant local or systemic adverse effect in recipients at the dosages and concentrations employed for treatment. Such carriers are generally known in the art. Suitable carriers for this invention are those conventionally used large stable macromolecules such as albumin, gelatin, collagen, polysaccharide, monosaccharides, polyvinyl-pyrrolidone, polylactic acid, polyglycolic acid, polymeric amino acids, fixed oils, ethyl oleate, liposomes, glucose, sucrose, lactose, mannose, dextrose, dextran, cellulose, mannitol, sorbitol, polyethylene glycol (PEG), and the like. Slow-release carriers, such as hyaluronic acid, may also be suitable. See particularly Prisell et al. (1992) *Int. J. Pharmaceu.* 85:51–56, and U.S. Pat. No. 5,166,331. Inclusion of hyaluronic acid and other polymers may have an additional beneficial effect on the IGF-I-responsive disorder osteoarthritis. See particularly Bragantini (1987) *Clin. Trials J.* 24(4):333–340; Dougados et al. (1993) *Osteoarthritis and Cartilage* 1:97–103; and Lussier et al. (1996) *J. Rheum.* 23:1579–1585; herein incorporated by reference. Other acceptable components in the composition include, but are not limited to, buffers that enhance isotonicity such as water, saline, phosphate, citrate, succinate, acetic acid, and other organic acids or their salts.

Preferred pharmaceutical compositions may incorporate buffers having reduced local pain and irritation resulting from injection of IGF-I compositions. Such buffers include, but are not limited to, low phosphate buffers and succinate buffers. For example, International Publication No. WO 94/15584 describes isotonic IGF-I solution at pH 5.5 to 6.5 with phosphate buffer present in an amount less than 50 mmol/L, which are reported to result in reduced pain upon injection. As another example, the pharmaceutical composition may comprise a succinate buffer with pH in the range of about 4.0 to about 7.5, and succinate in the range of 0.5 mM up to about 100 mM, preferably a range less than about 50 mM, as in the formulation disclosed in the copending application entitled "Injectable Formulation Containing Succinate," U.S. patent application Ser. No. 60/080,008, filed Apr. 3, 1998.

The pharmaceutical composition may additionally comprise a solubilizing agent or so-called solubility enhancer. Compounds containing a guanidinium group, most preferably arginine, are suitable solubility enhancers for IGF-I, as described above.

The method for formulating a pharmaceutical composition is generally known in the art. A thorough discussion of formulation and selection of pharmaceutically acceptable carriers, stabilizers, and isomolytes can be found in *Remington's Pharmaceutical Sciences* (18$^{th}$ ed.; Mack Pub. Co.: Eaton, Pa., 1990), herein incorporated by reference.

The pharmaceutical compositions comprising the concentrated IGF-I syrup, or IGF-I reconstituted from the IGF-I syrup, are useful in therapy directed to treatment of IGF-I responsive conditions. By "IGF-I-responsive condition" is intended any condition that responds in the short-term or in the long-term either positively or negatively to IGF-I. Such IGF-I-responsive conditions may be a normal condition. For example, a mammal may undergo IGF-I therapy to increase normal muscle mass where greater muscle mass is desirable, as in an athlete. In contrast, the IGF-I responsive condition may be an abnormal condition that is chronic, and thus occurs more or less continuously, or that is acute, as occurs following injury to a site, such as a joint or bone injury.

Conditions responsive to IGF-I include acute or chronic conditions including, but not limited to, hyperglycemic disorders, including all forms of diabetes; chronic lung disease; acute and chronic renal disorders; acute and chronic liver failure; hepatic cirrhosis; inflammatory responses, such as rheumatoid arthritis, psoriatic arthritis, Reiter's syndrome, and inflammatory bowel disease; short gut; ischemic injuries involving the heart, liver, or brain, or such as results from renal tubular necrosis; immunological disorders, such as immunodeficiencies including decreased immune tolerance or chemotherapy-induced tissue damage; organ rejection after transplantation; diseases or insufficiencies of cardiac structure or function, such as chronic heart conditions, cardiomyopathy, stroke, and congestive heart failure; growth retardation; osteoporosis; wound healing; bone damage; ophthalmic conditions; infertility; neurodegenerative disorders, such as motoneuron disease, multiple sclerosis, muscular dystrophy, diabetic neuropathy, demyelinating peripheral neuropathies, Parkinson's disease, Alzheimer's disease, and a sequela of traumatic spinal cord lesions; and articular cartilage disorders, such as osteoarthritis and trauma-related injuries. Any IGF-I-responsive disorder may benefit from administration of the pharmaceutical compositions comprising the IGF-I syrup or reconstituted IGF-I obtained therefrom of the present invention.

By "therapy" is intended treatment of an existing normal condition that is enhanced by IGF-I therapy, therapeutic treatment of an existing IGF-I-responsive abnormal condition, and preventive or prophylactic procedures performed before the occurrence of an abnormal disorder.

The pharmaceutical compositions comprising the IGF-I syrup or reconstituted IGF-I obtained therefrom may be used in therapy for IGF-I-responsive conditions of any mammal. Exemplary mammals include, but are not limited to, cats, dogs, horses, cows, sheep, pigs, and more preferably humans.

The highly concentrated syrup form of IGF-I disclosed in the present invention finds further use as an essentially water-free preparation of IGF-I. Thus, the methods of the present invention provide a means of preparing an essentially water-free IGF-I composition.

Being highly concentrated and essentially free of water, the IGF-I syrup is useful for preparing a dry powder form of IGF-I. Because little water must be removed from the IGF-I syrup during lyophilization as compared to solution formulations, the syrup form of IGF-I may be more efficiently dried in shorter periods of time. The resulting dry powder form of IGF-I is more densely packed (e.g., more IGF-I per unit volume) than other lyophilized IGF-I, and the preparation is low in salt content.

Being essentially free of water, the syrup form of IGF-I finds use in other processes that require the removal of water from protein compositions. For example, the IGF-I syrup could be used to encapsulate IGF-I in PLGA (poly(D,L-lactide-co-glycolide)) microspheres using the cryogenic process described by Johnson et al. (1996) Nature Medicine 2:795–799. See also the cryogenic process described in U.S. Pat. No. 5,019,400.

The following examples are offered by way of illustration and not by way of limitation.

EXPERIMENTAL

IGF-I for use in these experiments was recombinantly produced in the yeast strain Pichia pastoris and purified essentially as described in U.S. Pat. Nos. 5,324,639, 5,324,660, and 5,650,496 and International Publication No. WO 96/40776.

EXAMPLE 1

Solubility of IGF-I as a Function of pH

Following isolation, the solubility of recombinant human IGF-I (rhIGF-I) was determined by dialysis. A saturated rhIGF-I solution can be created by dialyzing rhIGF-I at high concentration (e.g., 100 mg/ml in pH 4.0 buffer) against conditions where rhIGF-I is less soluble. In this example, rhIGF-I (pH 4.0, 100 mg/ml) was dialyzed (3,000 molecular weight cutoff tubing) against three 20-fold volume changes of pH 6.0 buffer.

As rhIGF-I above the solubility limit partitioned, two phases formed, a layer of precipitated rhIGF-I and a solution phase containing a saturated solution of rhIGF-I. A sample of the solution phase rhIGF-I was removed and filtered through a 0.22 μm filter to remove any insoluble material. The concentration of the filtered rhIGF-I solution was then determined by UV spectroscopy using the known IGF-I absorption coefficient.

FIG. 1 shows rhIGF-I solubility as a function of pH. rhIGF-I remains very soluble below pH 5.0. A sharp decrease in solubility occurs between pH 5.0 and pH 5.5, with solubility above pH 5.5 being less than 10 mg/ml. When tonicifying salts are removed from buffer solution, solubility at pH 6.0 is only 3.0 mg/ml.

Although, IGF-I has an isoelectric point around pH 8.7, the solubility profile for rhIGF-I indicates the protein becomes much less soluble at solution pH well below that of its isoelectric point.

EXAMPLE 2

Preparation of IGF-I Syrup by Manipulation of Solution pH rhIGF-I as described in Example 1 was precipitated as follows. Bulk rhIGF-I at a concentration of 13 mg/ml was concentrated to 74 mg/ml in an initial buffer solution at pH 4.0 and then dialyzed in a 10 mM sodium citrate/140 mM sodium chloride buffer at pH 6.0 using spectra por tubing 1000 MWCO. The concentration of rhIGF-I remaining in solution was 10.6 mg/ml. Concentration of rhIGF-I in the initial and final solutions was measured spectrophotometrically in the uv region at 276 nm. The buffer solution was decanted off and the precipitated polypeptide recovered in the form of an opalescent viscous syrup. Concentration of rhIGF-I in the precipitated syrup form was determined at about 350 mg/ml of syrup.

The density of the rhIGF-I syrup was determined by weight at ambient temperature (23° C.). Ten milliliters (10 ml) of rhIGF-I syrup was prepared volumetrically and its weight determined on a Mettler AE240. The weight of the 10 ml sample of rhIGF-I syrup was determined to be 10.7 grams. Therefore, the density of the rhIGF-I syrup was determined to be 1.07 g/ml.

The viscosity of the rhIGF-I syrup was determined with a Cannon Instruments LV2000 Rotary Viscometer. The instrument was calibrated with a viscosity standard provided by the manufacturer. All measurements were performed at ambient temperature (23° C.). The viscosity of the rhIGF-I syrup was determined to be approximately 15,700 centipoise (cps).

EXAMPLE 3

Preparation of IGF-I Syrup by Removal of Solubility Enhancer

Figure 2:
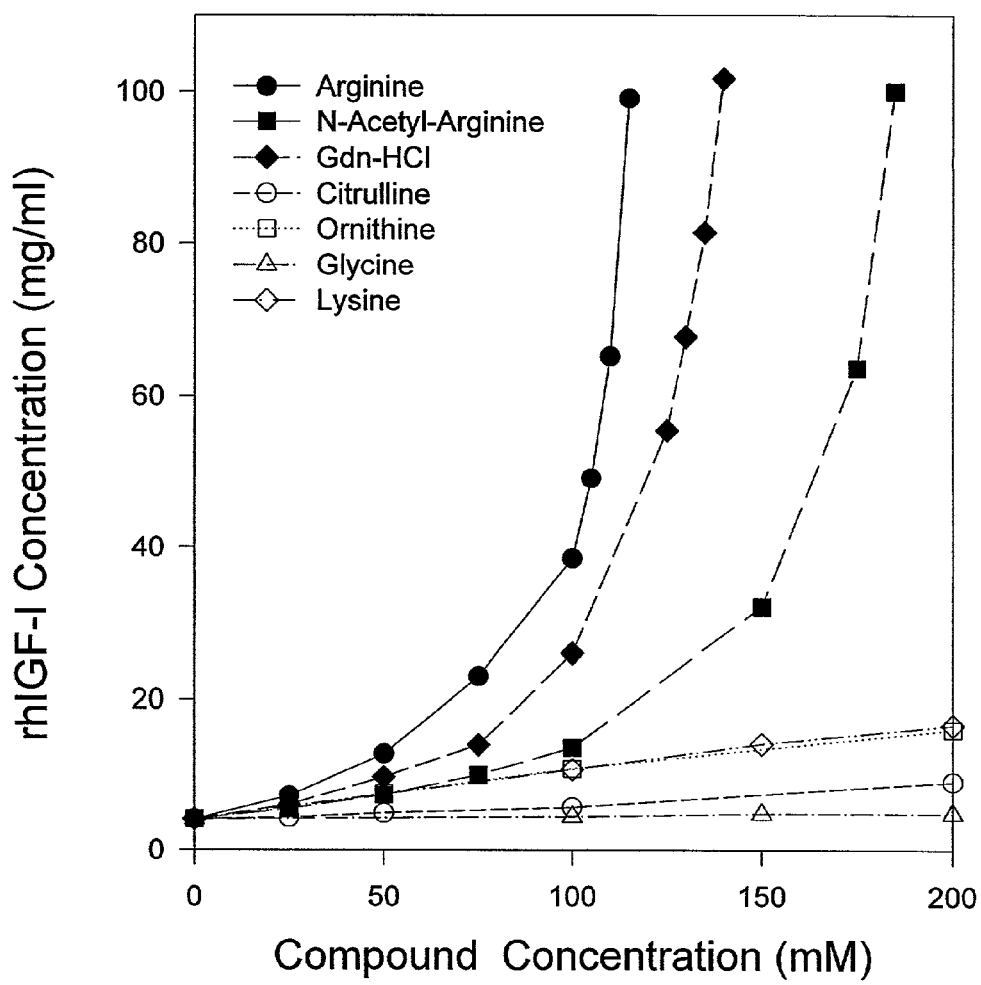
FIG. 2 shows rhIGF-I solubility as a function of the concentration of arginine or one of several other compounds, some of which have a guanidinium group and some of which do not.

Arginine and other compounds containing a guanidinium group have been shown to dramatically increase the solubility of IGF-I (see FIG. 2). In this example, arginine is used as a solubility enhancer to prepare a high concentration rhIGF-I solution from which the solubility enhancer is removed to precipitate the rhIGF-I syrup of the present invention.

For example, rhIGF-I at 100 mg/ml in 10 mM sodium citrate, 120 mM arginine, pH 6.0 is dialyzed against 10 mM sodium citrate, 140 mM sodium chloride, pH 6.0 at 4° C. Under these conditions, rhIGF-I is only soluble to about 10 mg/ml. Of the original 100 mg/ml, 90 mg/ml precipitates to form an opalescent syrup and 10 mg/ml remains in solution.

The soluble portion of the rhIGF-I can be decanted off and the rhIGF-I syrup recovered. This rhIGF-I syrup retains its biological activity.

EXAMPLE 4

Stability of IGF-I Syrup

A stability study was conducted with the highly concentrated, low salt-containing, biologically active syrup form of rhIGF-I. rhIGF-I was prepared by the method of Example 2. The precipitated rhIGF-I syrup was recovered. Buffer was layered on top of the syrup to allow a portion of the rhIGF-I to reconstitute. This buffer was free of any agents that would normally be used to promote protein refolding. A sample of this supernatant was removed at time zero (T=0 weeks), and the reconstituted rhIGF-I was analyzed by SDS-PAGE (Laemmli et al. (1970) *Nature* 227:680–685), RP-HPLC (Kunitani et al. (1986) *J. Chromatogr.* 359:391–402), and bioassay (Lopaczynski et al. (1993) *Regulatory Peptides* 48:207–216).

The syrup material was then stored at 4° C. After 2 weeks and 4 weeks, fresh buffer was layered on top of the syrup. The reconstituted material was analyzed again by SDS-PAGE, RP-HPLC, and bioassay. Results of this study are shown in Table 1.

These results show that rhIGF-I can be prepared by this method to form a viscous syrup and then reconstituted. These data also show that the reconstituted material retains its purity and activity.

TABLE 1

Stability of rhIGF-I Syrup

| Sample | Purity by RP-HPLC | Apparent Purity by SDS-PAGE | % Activity by Mitogenic Bioassay |
|---|---|---|---|
| Bulk rhIGF-I before precipitation T = 0 weeks | 95.6% | 100% | 104% |
| rhIGF-I after precipitation and resolubilization T = 0 weeks | 96.1% | 100% | 85% |
| rhIGF-I after precipitation and resolubilization T = 2 weeks | 95.0% | 100% | 105% |
| rhIGF-I after precipitation and resolubilization T = 4 weeks | 95.1% | 100% | 99% |

EXAMPLE 5

Preparation of Salt-Containing Precipitated Form of IGF-I

To 100 ml of rhIGF-I at 13.2 mg/ml in 0.1 M acetic acid (approximately pH 3.5), ammonium sulfate was added to 35% saturation at 4° C. The ammonium sulfate was dissolved with stirring, and the solution became "milky" white indicating that the rhIGF-I had precipitated from solution. The milky suspension was allowed to stir at 4° C. overnight, and the ammonium sulfate-precipitated rhIGF-I was recovered by centrifugation. The precipitated rhIGF-I, being more dense than the liquid, sedimented to the bottom of the centrifuge tube during centrifugation. The precipitated rhIGF-I was recovered by decanting the supernatant from the pellet. The recovered ammonium sulfate-precipitated rhIGF-I was unlike the IGF-I composition of the present invention; it was white in appearance (indicating the presence of substantial salt) and had the consistency of a thick paste rather than a flowable syrup.

EXAMPLE 6

Cryogenic PLGA Encapsulation Process Requiring Syrup Lyophilization

The rhIGF-I syrup of Example 2 or Example 3 is lyophilized and mixed with the PLGA in methylene chloride for encapsulation. The suspension so obtained is sprayed into liquid nitrogen and PLGA microspheres produced and recovered essentially as described by Johnson et al. (1996) *Nature Medicine* 2:795–799.

EXAMPLE 7

Cryogenic Process Not Requiring Syrup Lyophilization

The rhIGF-I syrup of Example 2 or 3 is filtered to remove substantially all water, is then mixed with a small quantity of ethanol, and is then added to PLGA dissolved in methylene chloride. Alternatively, the ethanol is present in methylene chloride. Ethanol mixed with the syrup extracts unbound water. This ethanol, being miscible with methylene chloride, partitions into the methylene chloride phase containing the PLGA polymer, thus facilitating practically the entire rhIGF-I in the syrup form to be encapsulated by the cryogenic process described by Johnson et al. (1996) *Nature Medicine* 2:795–799.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A low salt-containing aqueous composition comprising biologically active human IGF-I or a biologically active variant thereof in a concentration of about 250 mg/ml or greater and a pH of pH 5.0 or greater, wherein said variant is a polypeptide that has at least 80% amino acid sequence identity to the amino acid sequence of human IGF-I.

2. The composition of claim 1, wherein said human IGF-I or variant thereof is present in a concentration of about 250 mg/ml to about 500 mg/ml.

3. The composition of claim 1, wherein said human IGF-I or variant thereof is present in a concentration of about 350 mg/ml, and wherein said composition has a density of about 1.07 g/ml and a viscosity of about 15,700 cps.

4. A kit for reconstituting a pharmaceutical composition comprising biologically active human IGF-I or biologically active variant thereof, said kit comprising the composition of claim 1 and separately a pharmaceutically acceptable buffered solution having a pH less than or equal to pH 5.0.

5. A pharmaceutical composition comprising the composition of claim 1, and a pharmaceutically acceptable carrier.

6. The pharmaceutical composition of claim 5, wherein said composition is a sustained-release formulation.

7. The pharmaceutical composition of claim 5, wherein said composition is a gel formulation.

8. A cryogenically produced poly (D,L-lactide-co-glycolide) (PLGA) microsphere comprising the composition of claim 1.

9. The microsphere of claim 8, wherein said microsphere comprises a lyophilized form of said composition.

10. The composition of claim 1, wherein said variant differs from the amino acid sequence for said human IGF-I by up to 5 amino acid residues.

11. The composition of claim 1, wherein said variant differs from the amino acid sequence for said human IGF-I by up to 2 amino acid residues.

12. The composition of claim 1, wherein said variant differs from the amino acid sequence for said human IGF-I by one amino acid residue.

13. The composition of claim 1, wherein said human IGF-I is recombinant human IGF-I.

14. The composition of claim 13, wherein said recombinant human IGF-I is present at a concentration of about 250 mg/ml to about 500 mg/ml.

15. The composition of claim 13, wherein said recombinant human IGF-I is present at a concentration of about 350 mg/ml, and wherein said composition has a density of about 1.07 g/ml and a viscosity of about 15,700 cps.

16. A pharmaceutical composition comprising the composition of claim 1, and a pharmaceutically acceptable excipient.

17. The pharmaceutical composition of claim 16, wherein said composition is a sustained-release formulation.

18. The pharmaceutical composition of claim 16, wherein said composition is a gel formulation.

19. A low salt-containing aqueous composition comprising biologically active human IGF-I in a concentration of about 250 mg/ml or greater and a pH of pH 5.0 or greater.

20. The composition of claim 19, wherein said human IGF-I is recombinant human IGF-I.

21. The composition of claim 19, wherein said human IGF-I is present at a concentration of about 250 mg/ml to about 500 mg/ml.

22. The composition of claim 19, wherein said human IGF-I is present at a concentration of about 350 mg/ml, and wherein said composition has a density of about 1.07 g/ml and a viscosity of about 15,700 cps.

23. A pharmaceutical composition comprising the composition of claim 22, and a pharmaceutically acceptable carrier.

24. A cryogenically produced poly(D,L-lactide-co-glycolide) (PLGA) microsphere comprising the composition of claim 22.

25. A pharmaceutical composition comprising the composition of claim 22, and a pharmaceutically acceptable excipient.

26. A pharmaceutical composition comprising the composition of claim 19, and a pharmaceutically acceptable carrier.

27. A cryogenically produced poly(D,L-lactide-co-glycolide) (PLGA) microsphere comprising the composition of claim 19.

28. A pharmaceutical composition comprising the composition of claim 19, and a pharmaceutically acceptable excipient.

29. A low salt-containing aqueous composition comprising biologically active recombinant human IGF-I is a concentration of about 350 mg/ml, and wherein said composition has a density of about 1.07 g/ml and a viscosity of about 15,700 cps and a pH of pH 5.0 or greater.

30. A pharmaceutical composition comprising the composition of claim 29, and a pharmaceutically acceptable carrier.

31. A cryogenically produced poly(D,L-lactide-co-glycolide) (PLGA) microsphere comprising the composition of claim 29.

32. A pharmaceutical composition comprising the composition of claim 29, and a pharmaceutically acceptable excipient.

* * * * *